(12) United States Patent
Baudino et al.

(10) Patent No.: US 9,550,045 B2
(45) Date of Patent: Jan. 24, 2017

(54) REPOSITIONABLE THERAPY DELIVERY ELEMENT ANCHOR

(75) Inventors: Michael D. Baudino, Coon Rapids, MN (US); Brian T. Stolz, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 719 days.

(21) Appl. No.: 13/982,203

(22) PCT Filed: Jan. 24, 2012

(86) PCT No.: PCT/US2012/022408
§ 371 (c)(1),
(2), (4) Date: Oct. 1, 2013

(87) PCT Pub. No.: WO2012/103123
PCT Pub. Date: Aug. 2, 2012

(65) Prior Publication Data
US 2014/0155832 A1    Jun. 5, 2014

Related U.S. Application Data

(60) Provisional application No. 61/437,400, filed on Jan. 28, 2011.

(51) Int. Cl.
*A61M 25/04* (2006.01)
*A61M 25/02* (2006.01)
*A61N 1/05* (2006.01)

(52) U.S. Cl.
CPC ............ *A61M 25/04* (2013.01); *A61M 25/02* (2013.01); *A61N 1/05* (2013.01); *A61M 2025/0293* (2013.01)

(58) Field of Classification Search
CPC A61M 25/02; A61M 25/04; A61M 2025/024; A61M 2025/0246; A61M 2025/0248; A61M 2025/0293
See application file for complete search history.

(56) References Cited

U.S. PATENT DOCUMENTS 4,122,858 A    10/1978    Schiff
4,230,110 A    10/1980    Beroff
(Continued)

FOREIGN PATENT DOCUMENTS

DE    10015323 A1    11/2000
EP    0865799 A2    9/1998
(Continued)

OTHER PUBLICATIONS

International Search Report and Written Opinion of international application No. PCT/US2012/022408, dated Jan. 24, 2012, 12 pp.

*Primary Examiner* — Laura Bouchelle
(74) *Attorney, Agent, or Firm* — Shumaker & Sieffert, P.A.

(57) ABSTRACT

This disclosure includes an anchor configured to maintain a portion of a therapy delivery element within a desired location of a patient. The anchor comprises a body forming a lumen configured to compressibly engage the outer surface of the therapy delivery element to hold the anchor in place about the therapy delivery element. The anchor may be stretched such that the lumen becomes larger than the cross-section of the therapy delivery element to facilitate positioning the anchor about the therapy delivery element. The body forms two or more channels that facilitate radial stretching of the anchor using a pronged tool. Radially stretching the body via the channels using the pronged tool reduces a holding force of the anchor on the therapy delivery element to facilitate adjusting a position of the anchor relative to the therapy delivery element.

20 Claims, 7 Drawing Sheets

(56) References Cited

U.S. PATENT DOCUMENTS

| | | | |
|---|---|---|---|
| 4,435,174 A | 3/1984 | Redmond et al. | |
| 4,632,670 A | 12/1986 | Mueller, Jr. | |
| 4,672,979 A | 6/1987 | Pohndorf | |
| 4,676,782 A | 6/1987 | Yamamoto et al. | |
| 4,683,895 A | 8/1987 | Pohndorf | |
| 4,897,082 A | 1/1990 | Erskine | |
| 5,053,015 A | 10/1991 | Gross | |
| 5,267,969 A | 12/1993 | Goldhardt et al. | |
| 5,273,053 A | 12/1993 | Pohndorf | |
| 5,356,381 A | 10/1994 | Ensminger et al. | |
| 5,364,340 A | 11/1994 | Coll | |
| 5,476,493 A | 12/1995 | Muff | |
| 5,667,513 A | 9/1997 | Torrie et al. | |
| 5,683,446 A | 11/1997 | Gates | |
| 5,718,717 A | 2/1998 | Bontutti | |
| 5,746,722 A | 5/1998 | Pohndorf et al. | |
| 5,792,115 A | 8/1998 | Horn | |
| 5,843,146 A | 12/1998 | Cross, Jr. | |
| 5,927,277 A * | 7/1999 | Baudino | A61N 1/0539 600/386 |
| 5,957,968 A | 9/1999 | Belden et al. | |
| 6,078,839 A | 6/2000 | Carson | |
| 6,473,654 B1 | 10/2002 | Chinn | |
| 6,551,290 B1 | 4/2003 | Elsberry et al. | |
| 6,554,802 B1 | 4/2003 | Pearson et al. | |
| 6,743,209 B2 | 6/2004 | Brown et al. | |
| 6,901,287 B2 | 5/2005 | Davis et al. | |
| 6,997,919 B2 | 2/2006 | Olsen et al. | |
| 7,004,959 B2 | 2/2006 | Bonutti | |
| 7,090,661 B2 | 8/2006 | Morris et al. | |
| 7,591,970 B2 | 9/2009 | Olson | |
| 7,594,911 B2 | 9/2009 | Powers et al. | |
| 7,787,960 B2 | 8/2010 | Lubenow et al. | |
| 7,835,795 B2 | 11/2010 | Alexander et al. | |
| 2003/0199853 A1 | 10/2003 | Olsen et al. | |
| 2005/0101915 A1 | 5/2005 | Morris et al. | |
| 2005/0107744 A1 | 5/2005 | Morris et al. | |
| 2005/0261710 A1 | 11/2005 | Sakamoto et al. | |
| 2006/0084940 A1 | 4/2006 | Olsen et al. | |
| 2006/0084941 A1 | 4/2006 | Olsen et al. | |
| 2006/0195066 A1 | 8/2006 | Cross, Jr. | |
| 2007/0050005 A1 | 3/2007 | Lauro | |
| 2007/0078399 A1 | 4/2007 | Olson et al. | |
| 2008/0275401 A1 * | 11/2008 | Sage | A61M 25/02 604/175 |
| 2009/0125059 A1 | 5/2009 | Verzal et al. | |
| 2009/0248054 A1 * | 10/2009 | Sage | A61M 25/02 606/174 |

FOREIGN PATENT DOCUMENTS

| | | |
|---|---|---|
| WO | WO 0213714 A1 | 2/2002 |
| WO | WO 03090820 A1 | 11/2003 |
| WO | WO 2006037639 A1 | 4/2004 |
| WO | WO 2008088982 A1 | 7/2008 |
| WO | WO 2009120792 A2 | 10/2009 |

* cited by examiner

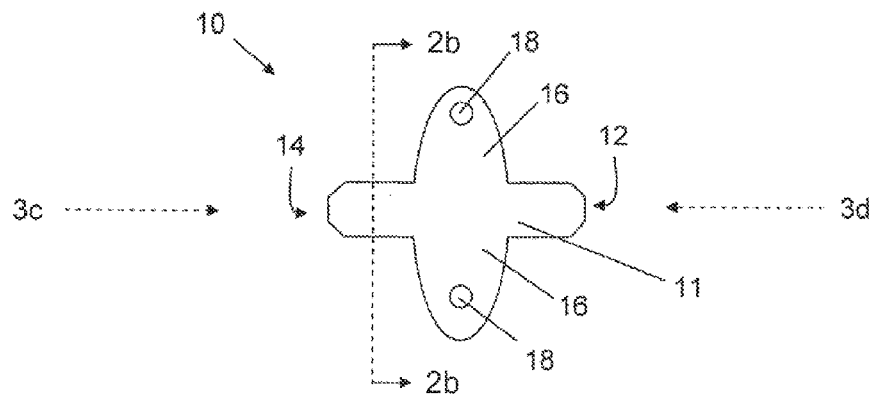
FIG. 2A
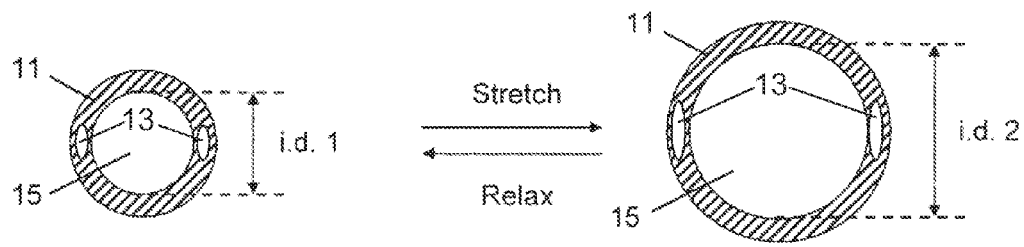
FIG. 2B
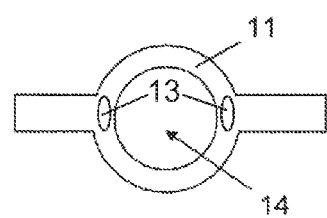 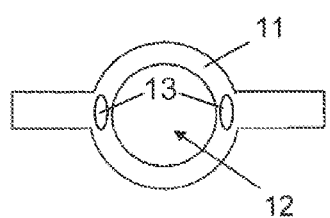
FIG. 2C  FIG. 2D

REPOSITIONABLE THERAPY DELIVERY ELEMENT ANCHOR

This application is a National Stage under 35 U.S.C. §371 of International Application No. PCT/US2012/022408, filed Jan. 24, 2012, which claims the benefit of U.S. Provisional Application 61/437,400, filed Jan. 28, 2011.

TECHNICAL FIELD

This disclosure relates to techniques for retaining a therapy delivery element, such as a catheter or a medical lead, relative to a position of a patient in which the therapy delivery element is implanted.

BACKGROUND

Therapy delivery elements such as implantable medical catheters and leads may be used for a variety of therapeutic and diagnostic purposes. Precise placement of therapy delivery elements may result in improved therapeutic efficacy or reduced side effects. Anchors may be attached to a therapy delivery element during implantation and sutured to subcutaneous tissue of the patient to secure a portion of the therapy delivery element in place.

SUMMARY

This disclosure describes repositionable anchors for therapy delivery elements, such as medical leads and catheters. As disclosed herein, an anchor for a therapy delivery element may include an elastic body that forms a lumen configured to compressibly engage the therapy delivery element when the anchor is disposed about the therapy delivery element. A repositionable anchor may further include at least two channels configured to receive distal ends of a pronged tool, such as a hemostat or modified hemostat, in order to facilitate radial stretching of the anchor using such a pronged tool. Radially stretching the anchor reduces a holding force of the anchor on the therapy delivery element and facilitates adjustment of the position of the anchor relative to the therapy delivery element.

In one example, this disclosure includes an anchor configured to maintain a portion of a therapy delivery element within a desired location of a patient. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery element. The body forms two or more channels that facilitate radial stretching of the anchor using a pronged tool. Radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

In another example, this disclosure includes a kit comprising a therapy delivery element, an anchor configured to maintain a portion of the therapy delivery element within a desired location of a patient. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery. The body forms two or more channels that facilitate radial stretching of the anchor using a pronged tool. Radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

In a further example, this disclosure includes a method for securing a therapy delivery element within a patient with an anchor. The anchor is configured to maintain a portion of the therapy delivery element within a desired location of a patient disposed about the therapy delivery element. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery element. The body forms two or more channels. The method comprises engaging the channels of the body with distal ends of a pronged tool and radially stretching the anchor with the pronged tool to reduce a holding force of the anchor on the therapy delivery element, and adjusting a position of the anchor relative to the therapy delivery element while radially stretching the anchor with the pronged tool.

The details of one or more examples of this disclosure are set forth in the accompanying drawings and the description below. Other features, objects, and advantages of this disclosure will be apparent from the description and drawings, and from the claims.

BRIEF DESCRIPTION OF DRAWINGS

FIGS. 2A-2D illustrate a repositionable anchor including channels that facilitate radial stretching of the anchor.

DETAILED DESCRIPTION

Figure 1:
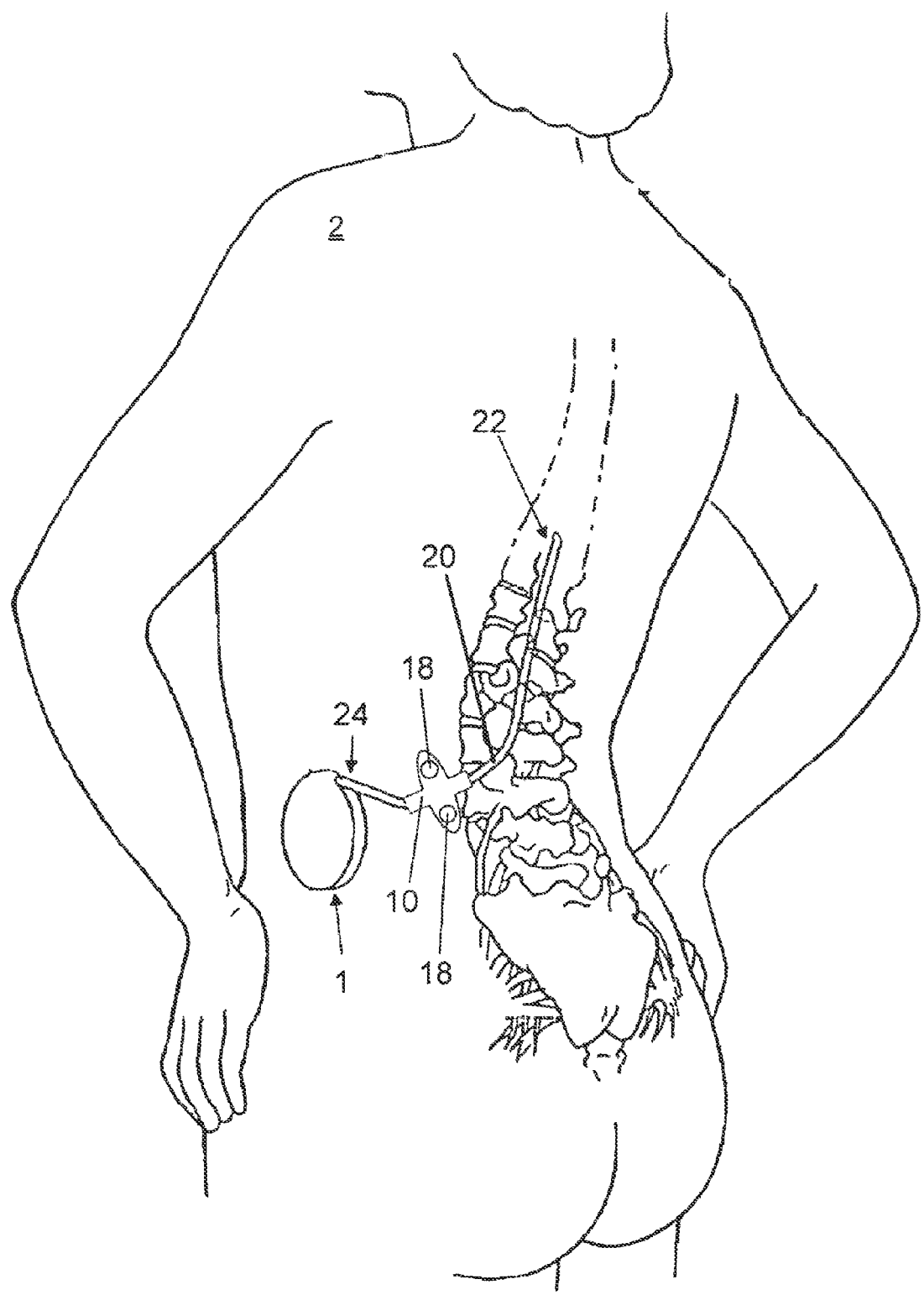
FIG. 1 is a conceptual illustration of an implantable medical system in a patient.

FIG. 1 illustrates an implantable medical device (IMD) 1 and a therapy delivery element 20. In different examples, IMD 1 may be an electrical stimulator, such as a neurostimulator, gastric stimulator, deep brain stimulator, a pacemaker, cardioverter-defibrillator, cochlear stimulation device, or the like. In other examples, IMD 1 may be a monitoring device, a fluid delivery device, or a device providing a combination of two or more of monitoring, fluid delivery and/or electrical stimulation. IMD 1 is subcutaneously implanted in patient 2, for example, in an abdominal region. A distal portion 22 of therapy delivery element 20 is positioned in patient 2 adjacent a target location for therapy and/or sensing. As shown in FIG. 1, in some examples, therapy delivery element 20 may be an elongated member such as an electrical stimulation lead or fluid delivery catheter. In the example depicted, distal portion 22 of therapy delivery element 20 is positioned within or along a spinal canal or cord of patient 2. In other examples, distal portion 22 of therapy delivery element 20 may be placed in any desired location to achieve its intended purpose, such as a diagnostic, monitoring, or therapeutic purpose. In the depicted example, proximal end 24 of therapy delivery element 20 is operably coupled to IMD 1.

In FIG. 1, an anchor 10 is shown disposed about therapy delivery device 20. Anchor 10 may be repositionable and may serve to anchor at least a portion of therapy delivery device 20 at a selected position within patient 2. As depicted, anchor 10 defines suture holes 18 for suturing the anchor 10 to tissue of the patient to maintain the position of the therapy delivery element 20 in proximity to the anchor 10 relative to a location of the patient. Anchor 10 includes a body formed from an elastic material that forms a lumen that receives therapy delivery element 20. The body of anchor 10 compressibly engages therapy delivery element 20 within the lumen as the interior wall of the lumen bears against the outer surface of the therapy delivery element with a compressive force. In this manner, anchor 10 is secured to therapy delivery element 20.

As described in further detail below, anchor 10 is deployable to a desired position along therapy delivery element using a rigid anchor deployment apparatus that fits within the body lumen of anchor 10 and holds the lumen in a stretched state. The anchor deployment apparatus includes a lumen that slidably receives therapy delivery element 20 such that anchor 10 can be positioned at a various locations along therapy delivery element 20 using the anchor deployment apparatus. Anchor 10 further includes channels (not shown in FIG. 1) that facilitate radial stretching of anchor 10 to allow a clinician to adjust the position of anchor 10 after it has been deployed from the anchor deployment apparatus. As one example, the channels may be configured to receive the distal ends of a hemostat or modified hemostat. In such an example, a clinician may engage the channels of anchor 10 with the distal ends of the hemostat and open the hemostat to decrease the holding force of the body lumen of anchor 10 on the outer surface of therapy delivery element 20 such that the clinician may slide anchor 10 along therapy delivery element 20.

Therapy delivery element 20 may be a catheter, a lead or lead extension, or the like. In different examples, therapy delivery element 20 may be an elongate element that can deliver stimulation therapy, deliver or withdraw fluid, sense a parameter, or diagnose a condition. Catheters are typically flexible tubes with a lumen running from the proximal end of the catheter to one or more delivery regions that are typically located at the distal portion of catheter. A proximal end of a catheter may be coupled to IMD 1 such that fluid may be delivered from the IMD 1 via the lumen of the catheter to a target location of a patient via one or more delivery regions of the catheter.

Leads typically may include one or more electrical contacts on a proximal end portion and one or more electrodes on a distal end portion. The contacts and electrodes are electrically coupled via electrically isolated wires running through the lead. The contacts may be electrically coupled to a port of IMD 1, and stimulation and/or sensing signals generated by IMD 1 may be carried along the lead and delivered to patient 2 via the electrodes. A lead may be connected to IMD 1 through a lead extension. A lead extension typically includes one or more contacts at the proximal and distal end portions that are electrically coupled through wires running through the extension.

FIGS. 2A-2D are schematic drawings of anchor 10. More specifically, FIG. 2A illustrates a top view of anchor 10. FIG. 2B illustrates a cross-section of anchor 10 taken through line 2b-2b. FIG. 2C illustrates a back view of anchor 10, and FIG. 2D illustrates a front view of anchor 10.

As shown in the top view of FIG. 2A, anchor 10 includes anchor body 11 with first opening 12 and second opening 14. Anchor body 11 may be formed of an elastomeric material, such as a biocompatible silicone material. In different examples, anchor body 11 may be formed using molding or extrusion operations. In addition or alternatively, anchor body 10 may be formed by one or more machining operations such as cutting, drilling and/or sanding. Lumen 15 extends through anchor body 11 from first opening 12 to second opening 14.

Referring to FIG. 2B, at least a portion of anchor body 11 is radially stretchable such that anchor body 11 has a first inner diameter (i.d. 1) (defined by the lumen 15) in a relaxed state and a second larger inner diameter (i.d. 2) in a stretched state. As used herein, radially stretchable means expandable such that a cross-sectional area of at least a portion of anchor body 11 is increasable, and is not limited to cylindrically shaped structures.

Anchor body 11 of anchor 10 may be formed from any suitable elastic material, such as a biocompatible silicone material. Other examples of suitable elastic materials include copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes, copolymers of polyurethane-silicon and the like. In various examples, anchor body 11 of anchor 10 is formed of material capable of being stretched up to about 5% or more without substantial tearing or plastic deformation. For example, anchor body 11 may be capable of being stretched up to about 20% or more, 50% or more, 75% or more, 100% or more, 150% or more, or 200% or more. For example, silicone is generally expandable up to about 100% or more without substantial tearing or plastic deformation. Anchor body 11 may be made from the same or different material than the remainder of anchor 10. In various examples, entire anchor 10 may be molded from the same material or anchor 10 may include an insert material, e.g., including gripping structures on the interior of lumen 15, and an overmold.

Figure 10:
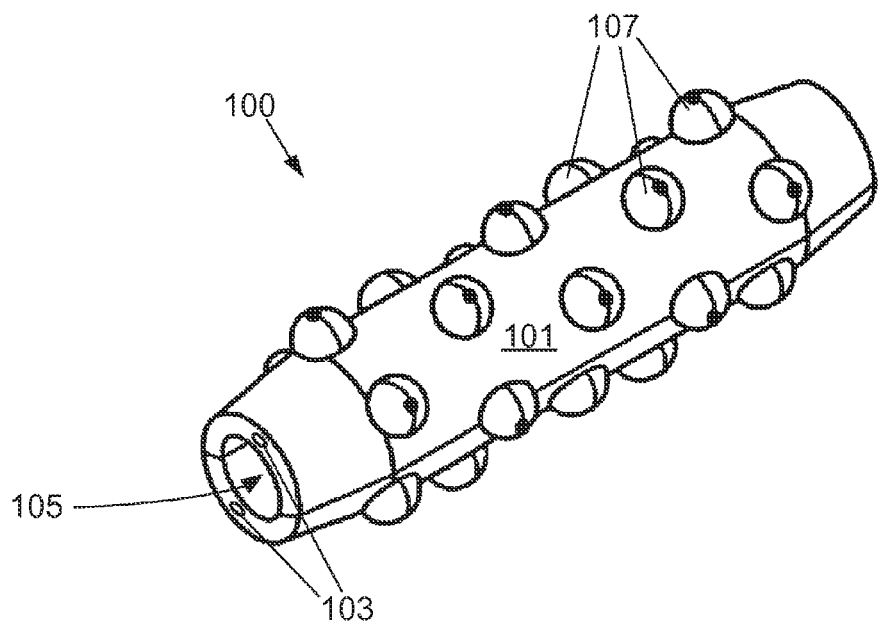

Anchor 10 depicted further includes retention elements 16, which form holes 18 for suturing anchor 10 to tissue of a patient. Retention element 16 may be coupled to or attached to (generally secured to) or may be integrally formed with anchor body 11. Anchor 10 may include any number of retention elements 16. While retention elements 16 are shown as wing-like extensions with suture holes 18, it will be understood that anchor 10 may include any suitable retention element, such as a plurality of bumps on an outer surface (as shown in FIG. 10) barbs, tines, or the like to retain anchor 10 within a tissue of a patient.

In various examples, anchor body 11 of anchor 10 further forms channels 13, which are configured to receive the distal ends of pronged took such as a hemostat or modified hemostat. Channels 13 allow a clinician to adjust the position of anchor 10 after it has been deployed from an anchor deployment apparatus. Specifically, a clinician may radially stretch anchor 10 by placing the distal ends of a hemostat within channels 13 and forcibly opening the hemostat. For example, a hemostat generally includes two distal prongs that pivot relative one another. A hemostat also generally includes proximal finger holes that facilitate manually separating and closing the distal prongs. To radially stretch anchor 10, a clinician may place the distal ends of a hemostat within channels 13 and forcibly separate the distal prongs by forcibly separating the proximal finger holes of the hemostat.

Radially stretching anchor 10 with the hemostat reduces the holding force of lumen 15 on a therapy delivery element such that the clinician may slide anchor 10 along the therapy delivery element while forcibly opening the hemostat. In the example of anchor 10, channels 13 extend through anchor 10 to allow a clinician to engage channels 13 from either end of anchor 10. In other examples, channels may not extend through anchor 10.

During a surgical procedure to implant a therapy delivery element and secure the therapy delivery element to a patient tissue with anchor 10, it may be useful to adjust the position of anchor 10 along the therapy delivery element after anchor 10 is deployed from the anchor deployment apparatus. For example, a clinician may like to slightly reposition anchor 10 along the longitudinal axis of the therapy delivery element in order to locate anchor 10 adjacent to a patient tissue most suitable for securing anchor 10. As another example, a clinician may reposition the distal end of the therapy delivery element, and then find it desirable to also reposition the relative position of anchor 10 on the therapy delivery element.

Figure 3A:
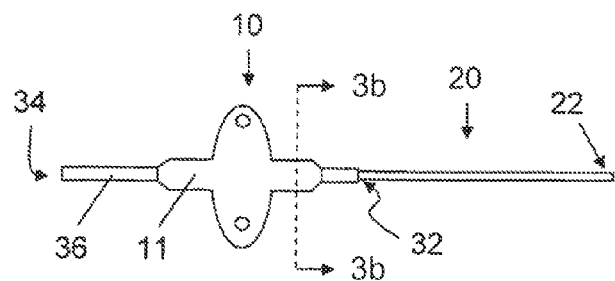
FIGS. 3A-3C illustrate an exemplary system including an anchor, an anchor deployment apparatus and a therapy delivery element.
Figure 3B:
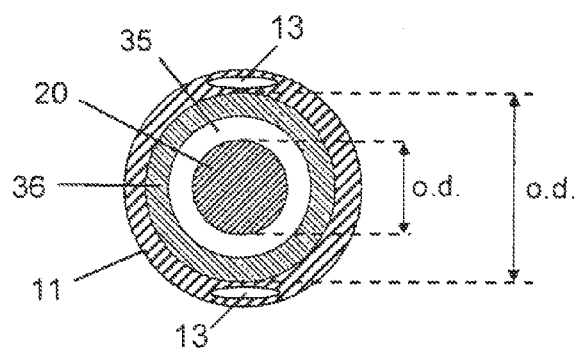
Figure 3C:
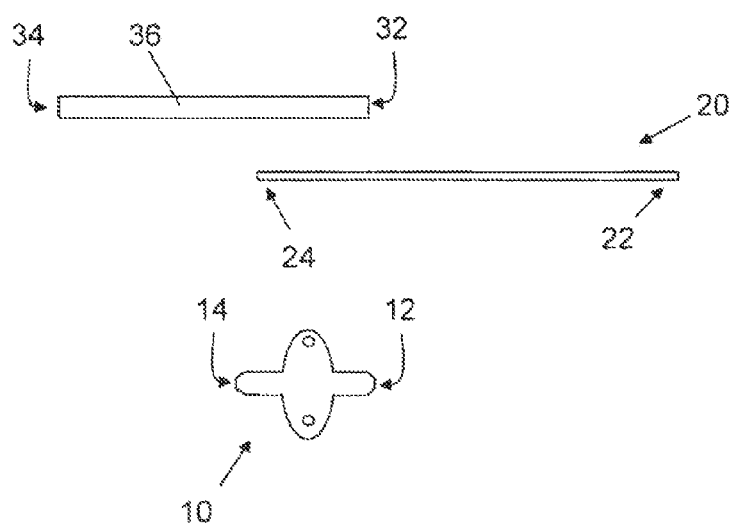

FIGS. 3A-3C illustrate an exemplary system including anchor 10, anchor deployment apparatus 36, and therapy delivery element 20. In particular, FIG. 3A illustrates a top view of the system, FIG. 3B illustrates a cross section taken through line 3b-3b of FIG. 3A, and FIG. 3C illustrates an exploded top view of the system.

Anchor deployment apparatus 36 forms lumen 35. Lumen 35 extends though anchor deployment apparatus 36 from proximal opening 34 to distal opening 32. Lumen 35 is configured to slidably receive proximal portion 24 of therapy delivery element 20. Anchor deployment apparatus 36 may be slid along therapy delivery element 20 such that proximal end 24 of therapy delivery apparatus 20 extends beyond proximal opening 34 of anchor deployment apparatus 36.

As depicted in FIGS. 3A and 3B, anchor 10 is disposed about anchor deployment apparatus 36. Elastic anchor body 11 of anchor 10 is disposed about and compressibly engages an outer surface of anchor deployment apparatus 36. Anchor deployment apparatus 36 has an outer diameter (o.d.) that is larger than the relaxed inner diameter (i.d. 1 see FIG. 2B) defined by lumen 15 of anchor 10 and that is smaller than a stretched inner diameter (i.d. 2, see FIG. 2B) defined by lumen 15 of anchor 10. As such, elastic anchor body 11 of anchor 10 is radially stretched with located on anchor deployment apparatus 36. The elastic properties of the material forming body 11 of anchor 10 allow body 11 to compressibly engage the outer surface of anchor deployment apparatus 36.

With reference to FIG. 3B, lumen 35 is configured to slidably receive at least a portion of therapy delivery element 20. Therapy delivery element 20 has an outer diameter (o.d.) that is larger than the relaxed inner diameter (i.d. 1, see FIG. 2B) defined by lumen 15 of anchor 10 and that is smaller than a stretched inner diameter (i.d. 2, see FIG. 2B) defined by lumen 15 of anchor 10. Therapy delivery element 20 is depicted in FIG. 3B as solid for purposes of illustration. In different examples, if therapy delivery element 20 were a catheter, a lumen might be depicted or if therapy delivery element 20 were a lead, an insulated conductor might be depicted.

Figure 4A:
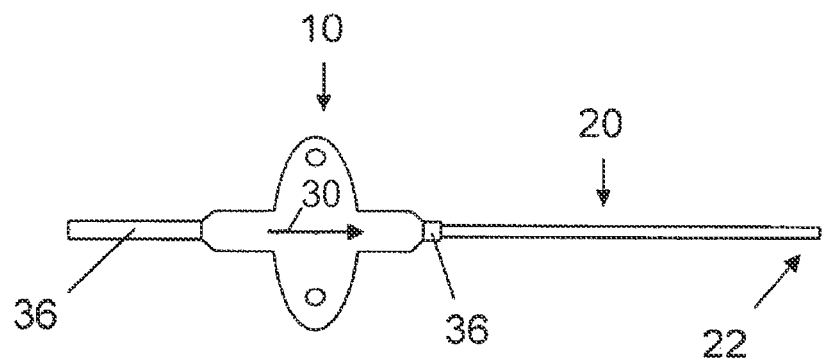
FIGS. 4A-4C are conceptual illustrations of deployment of an anchor from being disposed about an anchor deployment apparatus to disposed about a therapy delivery element.
Figure 4B:
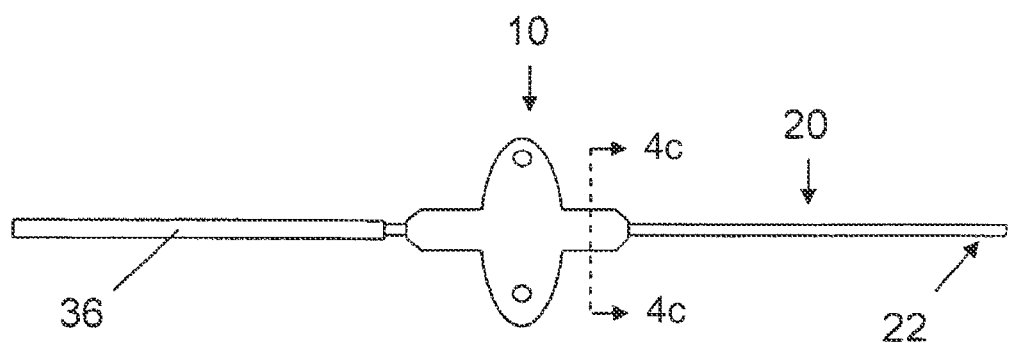
Figure 4C:
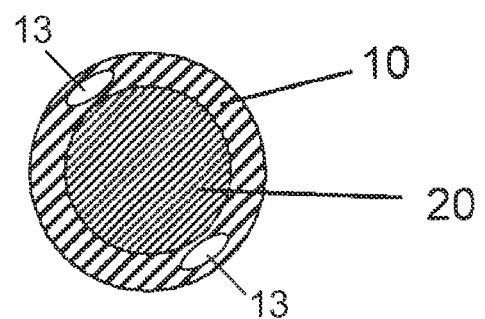

FIGS. 4A-4C are conceptual illustrations of deployment of anchor 10 from being disposed about anchor deployment apparatus 36 to disposed about therapy delivery element 20. FIG. 4A is the same top view of the system shown in FIG. 3A, except that anchor 10 is depicted as being moved distally (in direction of arrow 30) along anchor deployment apparatus 36. Anchor 10 is slidably moveable off distal end of anchor deployment apparatus 36 onto therapy delivery device 20, the proximal portion 24 of which is disposed within lumen 35 of anchor deployment apparatus 36. FIG. 4B illustrates anchor 10 disposed about therapy delivery element 20 after being deployed from anchor deployment apparatus 36.

Anchor 10 may be moved distally from anchor deployment apparatus 36 and onto therapy delivery element 20 through any acceptable manner, including by pushing. For example, anchor 10 may be manually moved by a clinician's fingers in some examples. In some examples, anchor 10 is pushed with an anchor engagement element. For example, suitable anchor engagement elements are disclosed in U.S. Pat. App. Pub. No. 2009/0248054, titled, "ANCHOR AND ANCHOR DEPLOYMENT APPARATUS," by Sage et al. When body member 11 of anchor 10 is disposed about therapy delivery element 20, body member snuggly engages at least a portion of the outer surface of therapy delivery element 20 (see e.g., FIG. 4C), due to elastic properties of body member 11 and the larger outer diameter of therapy delivery element 20 relative to the relaxed inner diameter of body member 11 defined by lumen 15.

Anchor body member 11 may grip therapy delivery element 20 with sufficient force to prevent movement of anchor 10 relative to therapy delivery element 20 under typical forces experienced when anchor 10 is disposed about a therapy delivery element 20 and is suture to a patient. In various examples, a pull force of about 1 pound-force (0.45 kilogram-force) or more is required to longitudinally move anchor 10 relative to a therapy delivery element 20 that anchor 10 is disposed about. For example, a pull force of about 2 pound-force (0.9 kilogram-force), about 3 pound-force (1.4 kilogram-force), about 4 pound force (1.8 kilogram-force), about 5 pound-force (2.3 kilogram-force), about 6 pound-pound force (kilogram-force), or more may be required to longitudinally move anchor 10 relative to therapy delivery element 20. In addition to the elastic properties of anchor body member 11, other material properties of anchor body 11 and therapy delivery element 20 may affect the pull force required to move anchor 10 along therapy delivery element 20. For example, friction due to various interactions may play a significant role.

If anchor 10 is to be sutured to tissue of a patient, it may be desirable to suture anchor 10 while it is disposed about anchor deployment apparatus 36 to prevent potential damage to therapy delivery element 20 due to accidental piercing of therapy delivery element 20 with a suture needle. Further, anchor deployment apparatus 36, due to the rigidity of anchor deployment apparatus 36, allows a clinician to maintain the location of anchor 10 with one hand and to suture anchor 10 with the other hand, if anchor 10 is sutured to tissue while disposed about anchor deployment apparatus 36, at least the proximal portion 24 of the therapy delivery element 20 may be disposed within lumen 35 of anchor deployment apparatus 36 to allow transfer of anchor 10 from anchor deployment apparatus 36 to therapy delivery element 20.

In some examples, the pull force required to move anchor 10 from anchor deployment apparatus 36 might be less than the pull force required to move anchor 10 relative to therapy delivery element 20. This can be accomplished, despite a larger outer diameter of anchor deployment apparatus 36 (relative to therapy delivery element 20) by forming anchor deployment apparatus 36 from material that decreases frictional interaction between anchor 10 and anchor deployment apparatus 36. For example, anchor deployment apparatus 36 may be formed of higher durometer material than therapy delivery element 20. By way of another example, anchor deployment apparatus 36 may be coated with a material to reduce friction, such ethylene tetrafluoroethylene (ETFE) or polytetrafluoroethylene (PTFE).

Anchor deployment apparatus 36 may be made of any suitable material. For example, anchor deployment apparatus 36 is formed from a rigid material, such as stainless steel, titanium, polycarbonate, polypropylene, or the like.

FIGS. 5-10 illustrate different exemplary repositionable anchors 50, 60, 70, 80, 90, 100, each including channels that facilitate radial stretching. Each of anchors 50, 60, 70, 80, 90, 100, is functionally similar to anchor 10, except that the anchors illustrated in FIGS. 5-10 may include different channel configurations than anchor 10. For example, each of anchors 50, 60, 70, 80, 90, 100 comprises a body formed from elastic material. In each of anchors 50, 60, 70, 80, 90, 100 the body forms a lumen extending from a first end of the body to a second end of the body. When in a relaxed state, a cross-section of the lumen is smaller than the cross-section of a therapy delivery element. The lumen is configured to be disposed about the outer surface of the therapy delivery element, and compressibly engage the outer surface of the therapy delivery element to hold the anchor in place about the therapy delivery element. The anchor may be stretched such that at least a portion of the lumen becomes larger than the cross-section of the therapy delivery element to facilitate positioning the anchor about the therapy delivery element. The body forms two or more channels that facilitate radial stretching of the anchor using a pronged tool. In addition, radially stretching the body via the channels using the pronged tool reduces a holding force of the anchor on the therapy delivery element when the anchor is disposed about the outer surface of the therapy delivery element by decreasing the surface area of the lumen that contacts the outer surface of the therapy delivery element. Reducing the holding force of the anchor on the therapy delivery element facilitates adjusting a position of the anchor relative to the therapy delivery element when the lumen is engaged with the outer surface of the therapy delivery element. Other details of anchors 50, 60, 70, 80, 90, 100 that are the same or similar to anchor 10 are readily apparent, and, for brevity, are not repeated with respect to anchors 50, 60, 70, 80, 90, 100.

Figure 5:
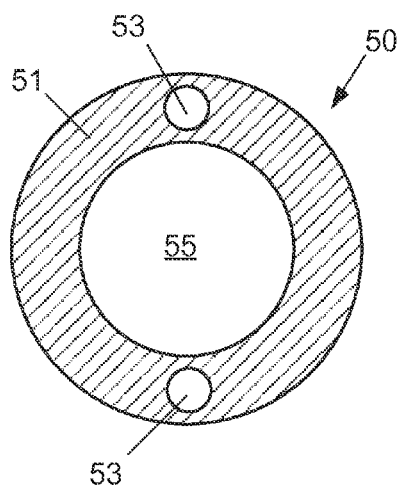
FIGS. 5-10 illustrate different exemplary repositionable anchors, each including channels that facilitate radial stretching.

FIG. 5 illustrates a cross-section of repositionable anchor 50. Anchor 50 includes body 51 forming lumen 55. Body 51 further forms two channels 53 that are lumens that are separate from lumen 55. Prongs of a tool such as a hemostat or modified hemostat may be inserted into channels 53. Channels 53 each provide an about round cross-section. Channels 53 facilitate radial stretching of anchor 50 using the pronged tool.

Figure 6:
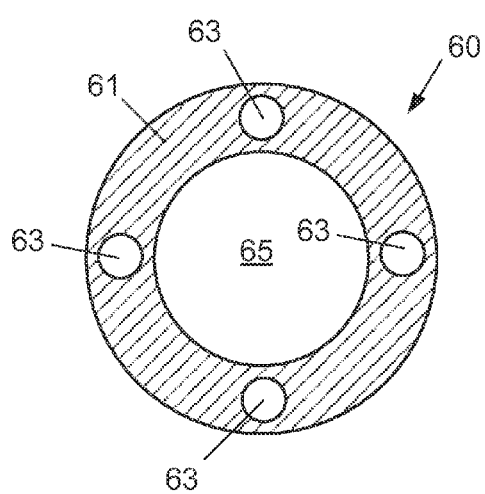

FIG. 6 illustrates a cross-section of repositionable anchor 60. Anchor 60 includes body 61 forming lumen 66. Body 61 further forms four channels 63 that are lumens that are separate from lumen 65. Channels 63 each provide an about round cross-section. Channels 63 facilitate radial stretching of anchor 60 using a pronged tool, such as a hemostat or modified hemostat. In one example, a pronged tool that may be used to radially stretch anchor 60 may resemble a four-pronged elastrator pliers. In another example, a hemostat may be used to radially stretch anchor 60 by inserting the distal ends of the hemostat in two of the four channels 63. For example, two of the four channels 63 may be selected depending on space, orientation and arrangement of anchor 60 and the therapy delivery element as positioned within the patient.

Figure 7:
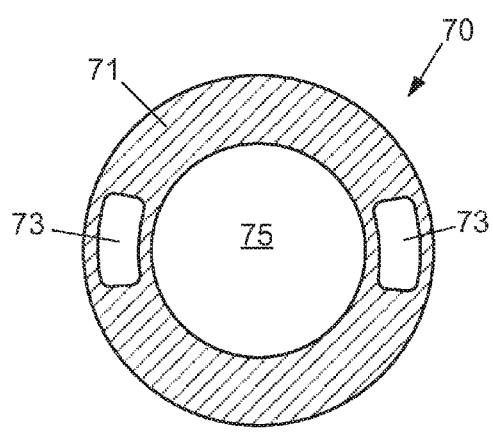

FIG. 7 illustrates a cross-section of repositionable anchor 70. Anchor 70 includes body 71 forming lumen 75. Body 71 further forms two channels 73 that are lumens that are separate from lumen 75. Channels 73 each provide an oblong cross-section. Channels 73 facilitate radial stretching of anchor 70 using a pronged tool, such as a hemostat or modified hemostat. A pronged tool used to radially stretch of anchor 70 may include round or oblong cross-section prongs. As compared to channels providing an about round cross-section, the oblong cross-section of channels 73 may better resist tearing of anchor 70 at channels 73 when anchor 70 is radially stretched with the pronged tool via channels 73.

Figure 8:
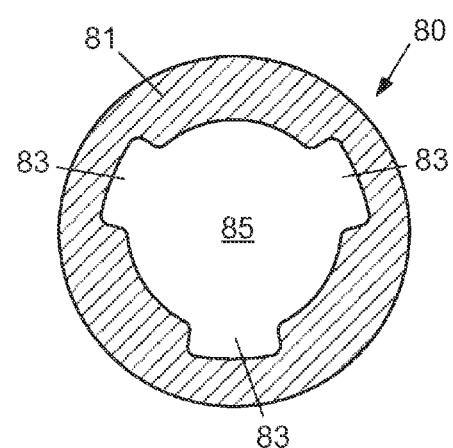

FIG. 8 illustrates a cross-section of repositionable anchor 80. Anchor 80 includes body 81 forming lumen 85. Lumen 85 includes three channels 83, each channel 83 providing an oblong cross-section. When anchor 80 is disposed about a therapy delivery element and lumen 85 is engaged with the therapy delivery element, the therapy delivery element does not fill channels 83, such that channels 83 may receive the distal ends of a pronged tool. Channels 83 facilitate radial stretching of anchor 80 using a pronged tool, such as a hemostat or modified hemostat. Such prongs may be inserted in two or more of channels 83 between the inner wall of lumen 85 of anchor body 81 and the outer surface of the body of the therapy delivery element. A pronged tool used to radially stretch of anchor 80 may include round or oblong prongs. As compared to channels providing an about round cross-section, the oblong cross-section of channels 83 may better resist tearing of anchor 80 at channels 83 when anchor 80 is radially stretched with the pronged tool via channels 83.

Figure 9:
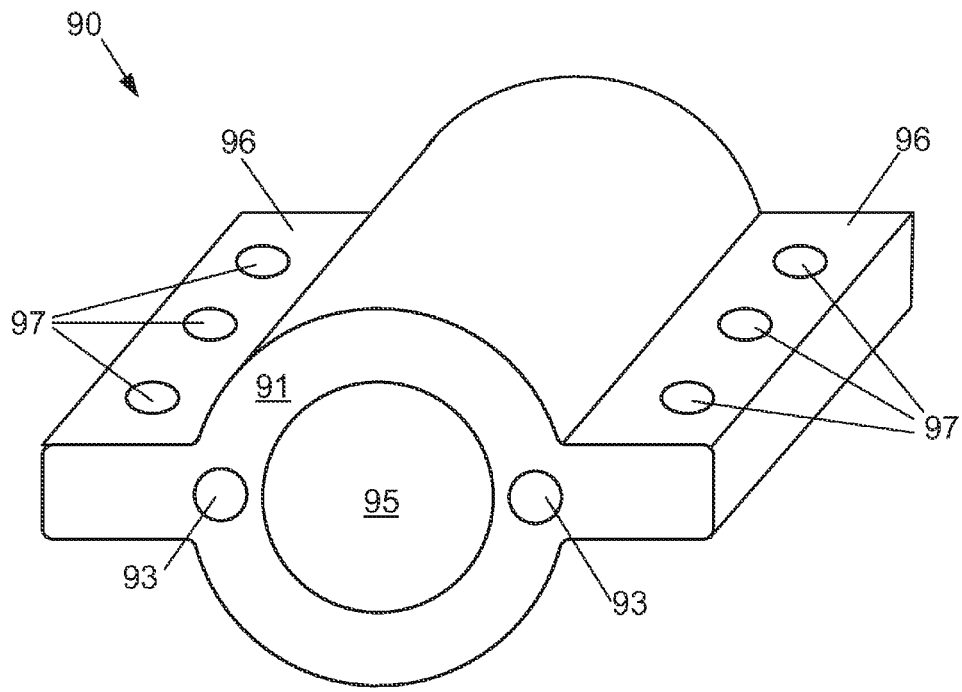

FIG. 9 illustrates a cross-section of repositionable anchor 90. Anchor 90 includes body 91 forming lumen 95. Anchor 90 also includes retention elements 96, which form holes 97 for suturing anchor 90 to tissue of a patient. As one example, anchor 90 may be substantially similar to anchor 10, except that retention elements 96 extend about the entire length of body 91. Body 91 further forms two channels 93 that are lumens that are separate from lumen 95. Channels 93 each provide an about round cross-section. Channels 93 facilitate radial stretching of anchor 90 using a pronged tool, such as a hemostat or modified hemostat. Channels 93 are positioned at about the same radial position as retention elements 16, and the material of retention elements 16 may support body 91 at channels 93 to resist tearing of anchor 90 when anchor 90 is radially stretched with the pronged tool via channels 93.

FIG. 10 illustrates repositionable anchor 100. Anchor 100 includes body 101 forming lumen 105. Body 101 further forms two channels 103 that are lumens that are separate from lumen 105. Channels 103 each provide an about round cross-section, although any of a variety of cross-section shapes may be used. Channels 103 facilitate radial stretching of anchor 100 using a pronged tool, such as a hemostat or modified hemostat.

The outer surface of anchor 100 includes a pattern of bumps 107. The bumps allow sutures to be placed in a constricting manner around the midportion of anchor 100. Bumps 107 are spheroidal in nature in the example of FIG. 10, but could assume other geometric shapes. In practice, a suture or sutures may be place circumferentially around the midportion of anchor 100 to secure anchor 100 to a tissue within a patient. Optionally, the body 101 may, alternatively or additionally, include radial grooves in the outer surface providing suture locations. In other examples, the pattern of bumps 107 may be combined with different repositionable anchor channel configurations, such as those illustrated in FIGS. 5-9.

Figure 11:
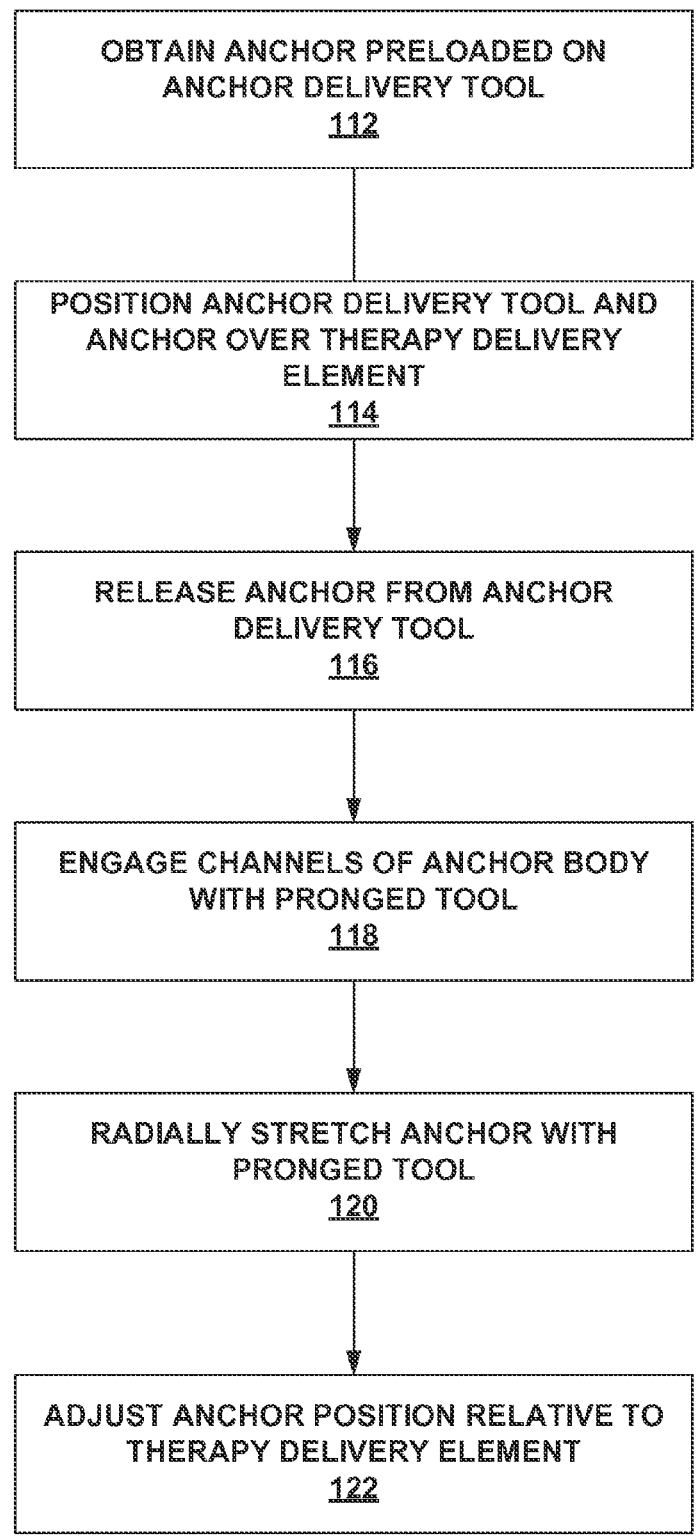
FIG. 11 is a flowchart illustrating techniques for implanting a therapy delivery element including adjusting a position of a repositionable anchor relative to the therapy delivery element.

FIG. 11 is a flowchart illustrating techniques for implanting a therapy delivery element including adjusting a position of a repositionable anchor relative to the therapy delivery element. As an example, the techniques of FIG. 11 may be performed by a clinician during an implant procedure for the therapy delivery element.

First, the clinician obtains a repositionable anchor pre-loaded on an anchor delivery tool (112). Then, the clinician positions the anchor on the therapy delivery element using the anchor deployment apparatus by sliding the anchor deployment apparatus over at least a portion of the therapy delivery element to a desired position within a body of a patient (114).

The clinician releases the anchor from the anchor deployment apparatus by sliding the anchor off the anchor deployment apparatus (116). In some examples, the clinician may push the anchor from the anchor deployment apparatus using an anchor engagement element.

If the clinician desires to reposition the anchor relative to the therapy delivery element, the clinician may engage channels of the body of the anchor with distal ends (prongs) of a pronged tool (118). By separating the prongs of the pronged tool, e.g., manually spreading the prongs apart by actuating proximal scissor arms of a hemostat, the clinician may radially stretch of the anchor to reduce a holding force of the anchor on the therapy delivery element (120). The holding force is reduced due to the reduced surface area of the lumen that contacts the outer surface of the therapy delivery element. For example, to radially stretch anchor 10, a clinician may place the distal ends of a hemostat within the channels and forcibly separate the distal prongs by forcibly separating the proximal finger holes of the hemostat. Reducing the holding force of the anchor on the therapy delivery element facilitates adjusting a position of the anchor relative to the therapy delivery element when the lumen is engaged with the outer surface of the therapy delivery element. The clinician may then adjust a position of the anchor relative to the therapy delivery element while radially stretching of the anchor with the pronged tool (122).

Once the clinician has positioned the anchor at a desired location relative to the therapy delivery element, the clinician may continue the implant procedure for the therapy delivery element. For example, the clinician may suture the anchor to a patient tissue to secure the portion of the therapy delivery element within the desired location of the patient. In addition, if the therapy delivery element is a medical lead, the clinician may implant a stimulator for delivering a medical therapy to the patient via the lead within the patient, and connect the stimulator to the lead. The clinician may also deliver therapy to the patient with the therapy delivery element, e.g., to test the therapy delivery element during the implant procedure.

Various examples of this disclosure have been described.

In one example, this disclosure is directed to an anchor configured to maintain a portion of a therapy delivery element within a desired location of a patient. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery element. The body forms two or more channels that facilitate radial stretching of the anchor using a pronged tool. Radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

In an example, the elastic material facilitates radially stretching the anchor body to expand at least a portion of the lumen from a first diameter in the relaxed state to a second diameter in which the portion of lumen is larger than the cross-section of the therapy delivery element without substantial tearing or plastic deformation of the anchor.

In an example, second diameter is at least about five percent greater than the first diameter.

In an example, channels extend from the first end of the body to the second end of the body.

In an example, the lumen is a first lumen, wherein the channels are lumens that are separate from the first lumen.

In an example, the lumen includes at least one of the channels, wherein the therapy delivery element does not fill the at least one of the channels when the lumen is engaged with the outer surface of the therapy delivery element.

In an example, the channels comprise three or more channels.

In an example, one or more of the channels provides an about round cross-section.

In an example, one or more of the channels provides an oblong cross-section.

In an example, the body of the anchor is formed of silicone.

In an example, the channels are configured to receive distal ends of a hemostat.

In an example, the anchor further comprises a plurality of bumps on an outer surface of the anchor.

In an example, the anchor further comprises a retention element forming a hole configured to facilitate suturing the anchor to tissue of a patient.

In an example, the body is configured to engage the outer surface of the therapy delivery element such that a pull force of 1 pound-force or more is needed to move the anchor along the outer surface of the therapy delivery element.

In another example, this disclosure is directed to a kit comprising a therapy delivery element, an anchor configured to maintain a portion of the therapy delivery element within a desired location of a patient. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery. The body forms two or more channels that facilitate radial stretching of the anchor using a pronged tool. Radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

In an example, the elastic material facilitates radially stretching the anchor body to expand at least a portion of the lumen from a first diameter in the relaxed state to a second diameter in which the portion of the lumen is larger than the cross-section of the therapy delivery element without substantial tearing or plastic deformation of the anchor.

In an example, the second diameter is at least about five percent greater than the first diameter.

In an example, the channels extend from the first end of the body to the second end of the body.

In an example, the lumen is a first lumen, wherein the channels are lumens that are separate from the first lumen.

In an example, the lumen includes at least one of the channels, wherein the therapy delivery element does not fill the at least one of the channels when the lumen is engaged with the outer surface of the therapy delivery element.

In an example, the channels comprise three or more channels.

In an example, the channels are configured to receive distal ends of a hemostat.

In an example, the anchor includes a plurality of bumps on an outer surface of the anchor.

In an example, the anchor includes a retention element forming a hole configured to facilitate suturing the anchor to tissue of a patient.

In an example, the therapy delivery element includes a catheter.

In an example, the kit further comprises a fluid delivery device for delivering a fluid to the patient via the catheter.

In an example, the therapy delivery element includes a lead including electrodes.

In an example, the kit further comprises a stimulator for delivering a medical therapy to the patient via the lead.

In an example, the kit further comprises the pronged tool including prongs, wherein the channels are configured to receive the prongs of the pronged tool.

In an example, the pronged tool includes a hemostat.

In an example, the kit further comprises an anchor deployment apparatus. The lumen of the anchor is stretchable to fit over the anchor deployment apparatus. The lumen of the anchor is a first lumen. The anchor deployment apparatus forms a second lumen configured to slidably receive at least a portion of the therapy delivery element such that when the anchor is disposed about the anchor deployment apparatus, the anchor and the anchor deployment apparatus may be freely positioned about the therapy delivery element.

In an example, the anchor is preloaded about the anchor deployment apparatus.

In an example, an outer surface of the anchor deployment apparatus is coated with a friction-reducing coating.

In an example, the friction-reducing coating is selected from a group consisting of; ethylene tetrafluoroethylene (ETFE), and polytetrafluoroethylene (PTFE).

In an example, the body member of the anchor is formed from silicone.

In an example, the therapy delivery element includes a catheter.

In another example, this disclosure is directed to a method for securing a therapy delivery element within a patient with an anchor. The anchor is configured to maintain a portion of the therapy delivery element within a desired location of a patient disposed about the therapy delivery element. The anchor includes a body comprising an elastic material. The body forms a lumen extending from a first end of the body to a second end of the body. The lumen is configured to be disposed about the outer surface of the therapy delivery element, and compressibly engage the outer surface of the therapy delivery element to hold the anchor in place about the therapy delivery element. When in a relaxed state, a cross-section of the lumen is smaller than a cross-section of the therapy delivery element at the outer surface of the therapy delivery element. The anchor may be stretched such that the lumen becomes larger than the cross-section of the therapy delivery element to facilitate positioning the anchor about the therapy delivery element. The body forms two or more channels. The method comprises engaging the channels of the body with distal ends of a pronged tool and radially stretching the anchor with the pronged tool to reduce a holding force of the anchor on the therapy delivery element, and adjusting a position of the anchor relative to the therapy delivery element while radially stretching the anchor with the pronged tool.

In an example, the pronged tool is a hemostat.

In an example, the method further comprises positioning the anchor on the therapy delivery element using an anchor deployment apparatus with the anchor preloaded on the anchor deployment apparatus. The lumen of the anchor is stretchable to fit over the anchor deployment apparatus. The lumen of the anchor is a first lumen. The anchor deployment apparatus forms a second lumen configured to slidably receive at least a portion of the therapy delivery element such that when the anchor is disposed about the anchor deployment apparatus, the anchor and the anchor deployment apparatus may be freely positioned about the therapy delivery element.

In an example, the method further comprises suturing the anchor to a patient tissue to secure the portion of the therapy delivery element within the desired location of the patient.

In an example, the elastic material facilitates radially stretching the anchor body to expand at least a portion of the lumen from a first diameter in the relaxed state to a second diameter in which the portion of the lumen is larger than the cross-section of the therapy delivery element without substantial tearing or plastic deformation of the anchor.

In an example, the second diameter is at least about five percent greater than the first diameter.

In an example, the lumen is a first lumen, wherein the channels are lumens that are separate from the first lumen.

In an example, the lumen includes at least one of the channels, wherein the therapy delivery element does not fill the at least one of the channels when the lumen is engaged with the outer surface of the therapy delivery element.

In an example, the body of the anchor is formed of silicone.

In an example, the anchor includes a plurality of bumps on an outer surface of the anchor.

In an example, the anchor includes a retention element forming a hole configured to facilitate suturing the anchor to tissue of a patient.

In an example, the therapy delivery element includes a catheter.

In an example, the therapy delivery element includes a lead including electrodes.

In an example, the method further comprises implanting a stimulator for delivering a medical therapy to the patient via the lead within the patient, and connecting the stimulator to the lead.

In an example, the method further comprises delivering therapy to the patient with the therapy delivery element.

What is claimed is:

1. An anchor configured to maintain a portion of a therapy delivery element within a desired location of a patient, the anchor comprising:
    a body comprising an elastic material,
    wherein the body forms a lumen extending from a first end of the body to a second end of the body,
    wherein the lumen is configured to be disposed about the outer surface of the therapy delivery element, and compressibly engage the outer surface of the therapy delivery element to hold the anchor in place about the therapy delivery element,
    wherein, when in a relaxed state, a cross-section of the lumen is smaller than a cross-section of the therapy delivery element at the outer surface of the therapy delivery element,
    wherein the anchor may be stretched such that the lumen becomes larger than the cross-section of the therapy delivery element to facilitate positioning the anchor about the therapy delivery element,
    wherein the body forms two or more channels that facilitate radial stretching of the anchor using a pronged tool,
    wherein the two or more channels are radially positioned on opposing sides of the lumen, and
    wherein radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

2. The anchor of claim 1, wherein the elastic material facilitates radially stretching the anchor body to expand at least a portion of the lumen from a first diameter in the relaxed state to a second diameter in which the portion of lumen is larger than the cross-section of the therapy delivery element without substantial tearing or plastic deformation of the anchor.

3. The anchor of claim 1, wherein the channels extend from the first end of the body to the second end of the body.

4. The anchor of claim 1, wherein the lumen is a first lumen, wherein the channels are lumens that are separate from the first lumen.

5. The anchor of claim 1, wherein the lumen includes at least one of the channels, wherein the therapy delivery element does not fill the at least one of the channels when the lumen is engaged with the outer surface of the therapy delivery element.

6. The anchor of claim 1, further comprising a plurality of bumps on an outer surface of the anchor.

7. The anchor of claim 1, wherein the body is configured to engage the outer surface of the therapy delivery element such that a pull force of 1 pound-force or more is needed to move the anchor along the outer surface of the therapy delivery element.

8. The anchor of claim 1, wherein the channels comprise three or more channels.

9. The anchor of claim 1, wherein the body is configured to engage the outer surface of the therapy delivery element such that a pull force of 1 pound-force or more is needed to move the anchor along the outer surface of the therapy delivery element.

10. A kit comprising:
    a therapy delivery element; and
    an anchor configured to maintain a portion of the therapy delivery element within a desired location of a patient,
    wherein the anchor includes a body comprising an elastic material,
    wherein the body forms a lumen extending from a first end of the body to a second end of the body,
    wherein the lumen is configured to be disposed about the outer surface of the therapy delivery element, and compressibly engage the outer surface of the therapy delivery element to hold the anchor in place about the therapy delivery element,
    wherein, when in a relaxed state, a cross-section of the lumen is smaller than a cross-section of the therapy delivery element at the outer surface of the therapy delivery element,
    wherein the anchor may be stretched such that the lumen becomes larger than the cross-section of the therapy delivery element to facilitate positioning the anchor about the therapy delivery element,
    wherein the body forms two or more channels that facilitate radial stretching of the anchor using a pronged tool,
    wherein the two or more channels are radially positioned on opposing sides of the lumen, and
    wherein radially stretching the body via the channels using the pronged tool reduces a holding force of the anchor on the therapy delivery element when the anchor is disposed about the outer surface of the therapy delivery element to facilitate adjusting a position of the anchor relative to the therapy delivery element when the lumen is engaged with the outer surface of the therapy delivery element.

11. The kit of claim 10, further comprising an anchor deployment apparatus,
wherein the lumen of the anchor is stretchable to fit over the anchor deployment apparatus,
wherein the lumen of the anchor is a first lumen,
wherein the anchor deployment apparatus forms a second lumen configured to slidably receive at least a portion of the therapy delivery element such that when the anchor is disposed about the anchor deployment apparatus, the anchor and the anchor deployment apparatus may be freely positioned about the therapy delivery element.

12. The kit of claim 11, wherein the anchor is preloaded about the anchor deployment apparatus.

13. The kit of claim 11, wherein an outer surface of the anchor deployment apparatus is coated with a friction-reducing coating.

14. The kit of claim 10, wherein the body includes a plurality of bumps on an outer surface of the body, and wherein the plurality of bumps are formed from the elastic material.

15. A method for securing a therapy delivery element within a patient with an anchor,
wherein the anchor is configured to maintain a portion of the therapy delivery element within a desired location of a patient disposed about the therapy delivery element,
wherein the anchor includes a body comprising an elastic material,
wherein the body forms a lumen extending from a first end of the body to a second end of the body,
wherein the lumen is configured to be disposed about the outer surface of the therapy delivery element, and compressibly engage the outer surface of the therapy delivery element to hold the anchor in place about the therapy delivery element,
wherein, when in a relaxed state, a cross-section of the lumen is smaller than a cross-section of the therapy delivery element at the outer surface of the therapy delivery element,
wherein the anchor may be stretched such that the lumen becomes larger than the cross-section of the therapy delivery element to facilitate positioning the anchor about the therapy delivery element,
wherein the body forms two or more channels radially positioned on opposing sides of the lumen,
wherein the method comprises:
engaging the channels of the body with distal ends of a pronged tool and radially stretching the anchor with the pronged tool to reduce a holding force of the anchor on the therapy delivery element; and
adjusting a position of the anchor relative to the therapy delivery element while radially stretching the anchor with the pronged tool.

16. The method of claim 15, further comprising:
positioning the anchor on the therapy delivery element using an anchor deployment apparatus with the anchor preloaded on the anchor deployment apparatus,
wherein the lumen of the anchor is stretchable to fit over the anchor deployment apparatus,
wherein the lumen of the anchor is a first lumen, and
wherein the anchor deployment apparatus forms a second lumen configured to slidably receive at least a portion of the therapy delivery element such that when the anchor is disposed about the anchor deployment apparatus, the anchor and the anchor deployment apparatus may be freely positioned about the therapy delivery element.

17. The method of claim 15, further comprising suturing the anchor to a patient tissue to secure the portion of the therapy delivery element within the desired location of the patient.

18. The method of claim 15, wherein the therapy delivery element includes a lead including electrodes, the method further comprising:
implanting a stimulator for delivering a medical therapy to the patient via the lead within the patient;
connecting the stimulator to the lead; and
delivering therapy to the patient with the therapy delivery element.

19. The method of claim 15, wherein the pronged tool is a hemostat.

20. The method of claim 15, wherein the body includes a plurality of bumps on an outer surface of the body, wherein the plurality of bumps are formed from the elastic material.

* * * * *